(12) United States Patent
Yachia et al.

(10) Patent No.: US 8,292,939 B2
(45) Date of Patent: Oct. 23, 2012

(54) SYSTEM AND METHOD FOR DELIVERING A MEDICAL DEVICE TO A BODY LOCATION

(75) Inventors: Daniel Yachia, Herzliya (IL); Shay Galili, Tel Aviv (IL); Ilan Lemerovitch, Hertzelya (IL)

(73) Assignee: Allium Ltd (IL)

( * ) Notice: Subject to any disclaimer, the term of this patent is extended or adjusted under 35 U.S.C. 154(b) by 209 days.

(21) Appl. No.: 12/065,787

(22) PCT Filed: Sep. 6, 2006

(86) PCT No.: PCT/IL2006/001029
§ 371 (c)(1),
(2), (4) Date: Jun. 26, 2008

(87) PCT Pub. No.: WO2007/029242
PCT Pub. Date: Mar. 15, 2007

(65) Prior Publication Data
US 2008/0319524 A1    Dec. 25, 2008

(30) Foreign Application Priority Data
Sep. 6, 2005 (IL) .......................................... 170698

(51) Int. Cl.
*A61F 2/06* (2006.01)

(52) U.S. Cl. ...................................... 623/1.11; 606/108

(58) Field of Classification Search .................. 623/1.11; 604/95.01, 156, 158–161, 164.05; 606/108, 606/191, 194, 200
See application file for complete search history.

(56) References Cited

U.S. PATENT DOCUMENTS

| 5,261,887 | A | * | 11/1993 | Walker ........................... 604/161 |
| 5,529,225 | A | * | 6/1996 | Chang ............................ 222/391 |
| 5,868,755 | A | * | 2/1999 | Kanner et al. ................. 606/108 |
| 5,944,727 | A | * | 8/1999 | Ahari et al. .................... 606/108 |
| 6,159,198 | A | | 12/2000 | Gardeski et al. |
| 6,221,081 | B1 | | 4/2001 | Mikus et al. |
| 6,391,051 | B2 | | 5/2002 | Sullivan et al. |
| 6,517,569 | B2 | | 2/2003 | Mikus et al. |
| 6,599,296 | B1 | * | 7/2003 | Gillick et al. ................. 606/108 |
| 7,326,203 | B2 | * | 2/2008 | Papineau et al. ................. 606/41 |
| 2002/0123755 | A1 | * | 9/2002 | Lowe et al. .................. 606/108 |
| 2002/0165554 | A1 | | 11/2002 | Dworschak et al. |

FOREIGN PATENT DOCUMENTS

| WO | 9820812 A1 | 5/1998 |
| WO | 03074120 A1 | 9/2003 |
| WO | 2004066809 A2 | 8/2004 |

* cited by examiner

*Primary Examiner* — Kathleen Sonnett
*Assistant Examiner* — Sarah Webb
(74) *Attorney, Agent, or Firm* — Brooks Kushman P.C.

(57) ABSTRACT

A system for delivering a medical device to a body location. The system includes a sheath (6) having a distal end (10) configured to receive the medical device (18). An actuating mechanism (16) causes the sheath to slide proximally upon which it becomes slit at its proximal (8) end longitudinally by blades (41) to expose the medical device.

13 Claims, 7 Drawing Sheets

SYSTEM AND METHOD FOR DELIVERING A MEDICAL DEVICE TO A BODY LOCATION

FIELD OF THE INVENTION

This invention relates to systems for delivering a medical device, such as a stent, to a body location.

BACKGROUND OF THE INVENTION

Medical devices that are deployed at a site inside the body must be delivered to the site. For example, stents are cylindrical devices used to maintain the patency of a body passageway, such as a blood vessel or a urethra. A stent is delivered to the location where it is to be deployed on the distal end of a delivery device such as a catheter. During delivery, the stent is maintained in a small caliber conformation. After delivery to the site of deployment, the stent is made or allowed to expand so as to assume a large caliber conformation in the body passageway. Some stents are "self-expanding", in which case the stent in the large caliber conformation is mechanically restrained in the small caliber conformation in which it is delivered to the site of deployment. After delivery, the restraint is removed so as to allow the stent to assume its large caliber conformation at the site of deployment. It is also known to form a stent from a one-way or two-way shape memory alloy, such as Nitinol™. With this type of stent, the stent is brought from one caliber to another by exposing the stent to a change of temperature, as is known in the art of shape memory stents. Balloon expandable stents, made of a non-shape memory material such as stainless steel, are also known.

U.S. Pat. Nos. 6,221,081 and 6,517,569 to Mikus et al disclose an insertion device in which a stent is mounted onto the distal end of an inner sheath. The stent is surrounded by a "peel-away sheath", which in turn is surrounded by an outer sheath. After the distal end of the device has been delivered to a body site where the stent is to be deployed, the outer sheath is retracted. The stent is then allowed to assume its large caliber conformation. The "peel-away sheath" is then grasped and manually split by the user as the "peel-away sheath" is removed.

U.S. Pat. No. 6,159,198 to Gardeski et al. discloses an introducing system for introducing electric leads to a body site. The introducer has a hollow sheath through which the leads are delivered to a body site. After the leads have been delivered, the sheath is manually retracted from the body. As the sheath is pulled out of the body it encounters a blade that cuts the sheath longitudinally from its proximal end to its distal end.

SUMMARY OF THE INVENTION

In its first aspect, the present invention provides a delivery system for delivering a stent to a body site. The stent delivery system of the invention has a grasping handle from which extends a slender hollow sheath. The tube has a diameter configured to allow a stent to be mounted onto the tube in its small caliber conformation. The tube is contained in the lumen of a cylindrical sheath formed from a soft pliant material such as Teflon, so that a stent mounted on the tube is covered by the sheath.

Within the grasping handle is an actuating mechanism, for causing proximal movement of the sheath over the tube so as to expose a stent mounted on the distal end of the sheath. As the sheath slides proximally under the influence of the actuating mechanism, the proximal end of the sheath encounters one or more blades. The blades are positioned in the grasping handle so as to slit the sheath longitudinally from its proximal end to its distal end as the sheath slides proximally over the sheath. The cut portion may accumulate inside a compartment or may exit the grasping handle.

In one embodiment of the invention, the actuating mechanism includes a trigger and one or more friction clamps. The friction clamps are coupled to the trigger so that, when the trigger is depressed, the friction clamps firmly grasp the sheath and cause the sheath to be displaced proximally over the tube. The trigger is spring biased in its released position. When the trigger subsequently returns to its released position, the friction clamps assume a non-engaging configuration in which the sheath is released from the grasp of the friction clamps so as to prevent movement of the sheath over the tube. Repeated cycles of depressing and releasing the trigger therefore cause a cumulative proximal sliding of the sheath along the tube and into the blades.

In its second aspect, the invention provides a method for delivering a stent to a body location. In accordance with this aspect of the invention, a stent in its small caliber conformation is mounted onto the distal end of the tube of the delivery system of the invention. The tube and stent are then covered with the sheath of the delivery system. The distal end of the sheath is then delivered to a body site where the stent is to be deployed. The actuating mechanism is then used to cause proximal movement of the sheath over the tube. As the sheath moves proximally over the tube, the tube is engaged by the blades which slit the tube from its proximal end to its distal end. The proximal movement of the tube, and the slitting of the tube by the blades, continue until the distal end of the tube has completely slid over the stent and the stent is no longer covered by the tube. The stent is then allowed to assume its large caliber configuration in which it is to be deployed in the passageway. After deployment of the stent, the tube is removed from the body.

Thus, in its first aspect, the invention provides a system for delivering a medical device to a body location, comprising:

(a) a sheath having a proximal end and a distal end, the distal end being configured to receive the medical device;

(b) one or more blades; and (c) an actuating mechanism capable of causing the sheath to slide proximally and be slit at its proximal end longitudinally by the one or more blades and to expose the medical device.

In its second aspect, the invention provides a method for delivering a medical device to a body location; comprising:

(a) Providing a system for delivering a medical device to a body location, the system comprising:

(i) a sheath having a proximal end and a distal end, the distal end being configured to receive the medical device;

(ii) one or more blades; and (iii) an actuating mechanism capable of causing the sheath to slide proximally and be slit at its proximal end longitudinally by the one or more blades and to expose the medical device;

(b) inserting the medical device into the distal end of the sheath;

(c) delivering the distal end of the sheath and the medical device to the body location; and (d) actuating the actuating mechanism to cause the sheath to slide proximally and be slit at its proximal end longitudinally by the one or more blades and to expose the medical device at the body location.

BRIEF DESCRIPTION OF THE DRAWINGS

In order to understand the invention and to see how it may be carried out in practice, a preferred embodiment will now be described, by way of non-limiting example only, with reference to the accompanying drawings, in which.

DETAILED DESCRIPTION OF THE INVENTION

Figure 1:
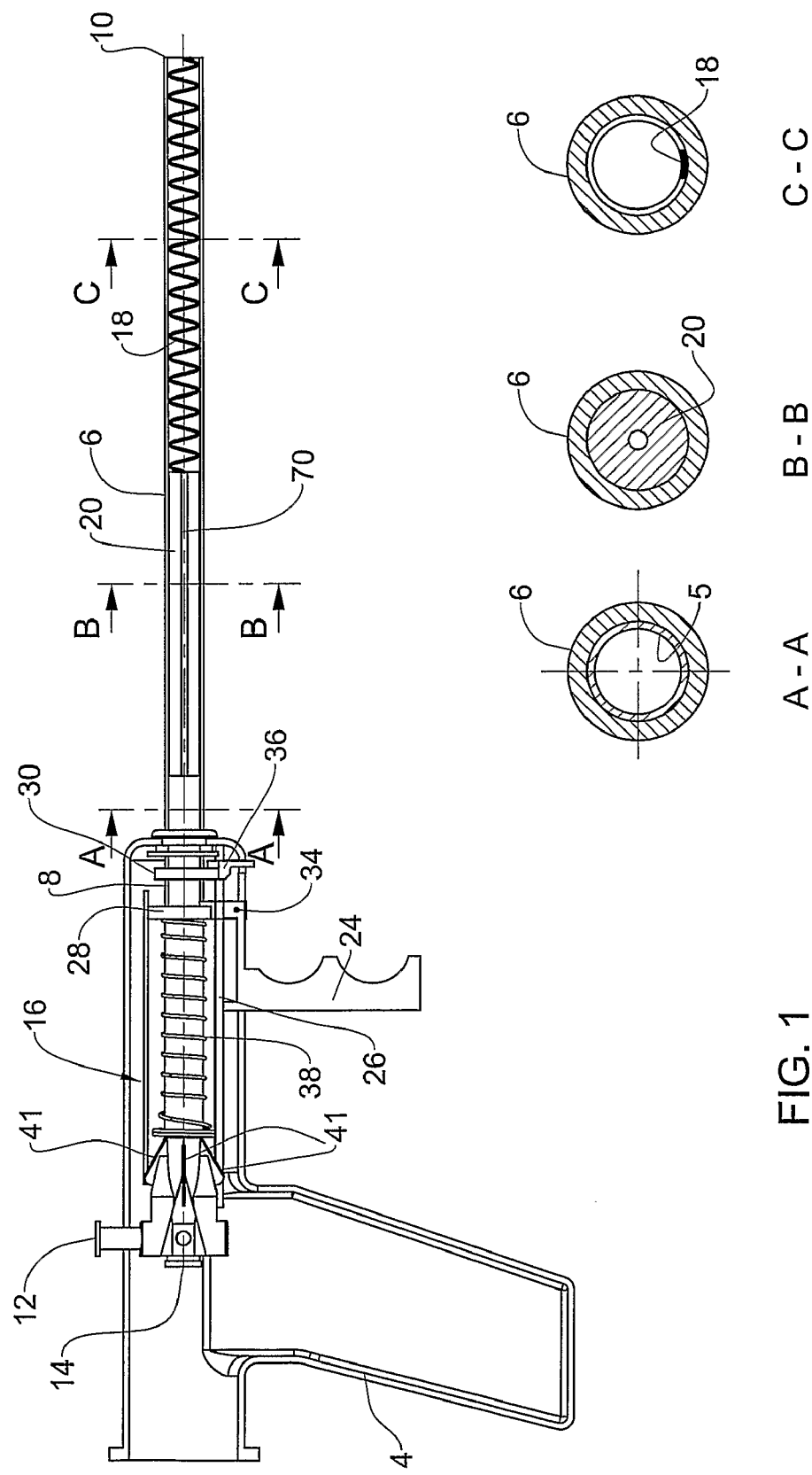
FIG. 1 shows a system for delivering a medical device to a body location according to a first embodiment of the invention.

FIG. 1 shows a delivery system 2 for delivering a medical device 18, to a body location, in accordance with one embodiment of the invention. Although the system 2 is shown with the medical device 18 being a stent, this is by way of example only, and the system 2 may be used to deliver any medical device such as an electrode, or a uretheral shield.

The delivery system 2 has a grasping handle 4. A slender hollow sheath 6, having a proximal end 8, initially located inside the grasping handle 4, and a distal end 10, has an inner diameter configured to allow the stent 18 in its small caliber conformation or another medical device to be contained inside the distal end of the sheath 6. The proximal end 8 of the sheath is mounted on a rigid or flexible tube 5 located in, and extending from, the grasping handle 4. In the lumen of the sheath 6, between the tip of the tube 5 and the medical device 18 is a spacing rod 20 having an axial channel 7. The tube 5 is provided with a first fitting 12 for connection to a fluid source such as water or saline, for delivering the fluid to the distal end of the sheath 6 via the lumen of the tube 5 and the channel 7. The tube 5 is also provided with a second fitting 14 for attachment to an optical element (not shown) for viewing a body region in the vicinity of the distal end 10. Within the housing of the grasping handle 4, is an actuating mechanism, generally indicated by 16, for retracting the sheath 6 proximally so as to uncover the medical device 18, as explained in detail below.

The sheath 6 is formed from a soft pliant material such as Teflon or polycarbonate. In the case that the medical device 18 is a self-expanding stent, the sheath 6 may serve to restrain the stent in its narrow caliber configuration until it is to be deployed in the body. The insert to FIG. 1 shows cross sections of the sheath 6, at the plane AA, BB, and CC.

When the medical device 18 has been delivered to a body location where it is to be deployed, the actuating mechanism 16 is used to retract the sheath 6 in a proximal direction so as to expose the medical device 18. The actuating mechanism 16 includes a trigger 24 that is slidable along a track 26 from a released position shown in FIG. 1, via an intermediate position shown in FIG. 2, to a depressed position shown in FIG. 3. The activating mechanism 16 also includes two friction clamps 28 and 30. The friction clamps 28 and 30 are shown enface in the insert to FIG. 2. The friction clamps 28 and 30 have a hole 32 and 33, respectively, dimensioned to allow the sheath 6 to pass through the friction clamps 28 and 30. The friction clamp 28 is attached to the trigger 24 at a pivot 34. The friction clamp 30 is attached to the housing of the grasping handle at a pivot 36. This allows the friction clamp 28 to rotate about the pivots 34 and 36 respectively, in a clockwise direction when viewed in the perspective of FIGS. 1 to 3 from the straight position shown in FIG. 1 to a tilted position shown in FIG. 2. The friction clamps 28 and 30 are prevented form rotating about the pivots 34 and 36 respectively, in a counterclockwise direction when viewed in the perspective of FIGS. 1 and 2 from the straight position shown in FIG. 1 due to the fact that the pivots 34 and 36 are located on the distal side of the friction clamps 28 and 30.

Figure 2:
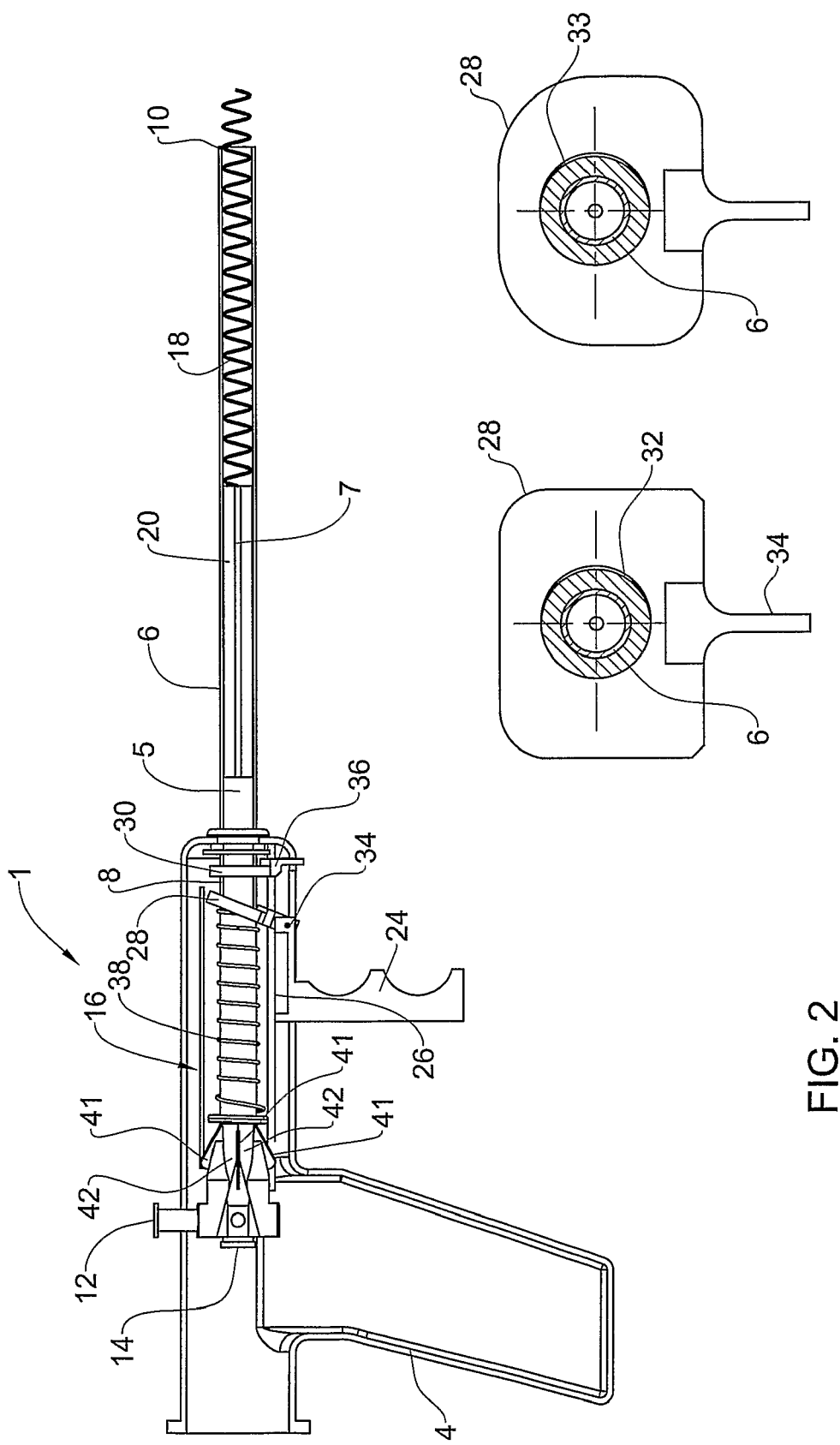
FIG. 2 shows the embodiment of FIG. 1 in an early stage of actuation.
Figure 3:
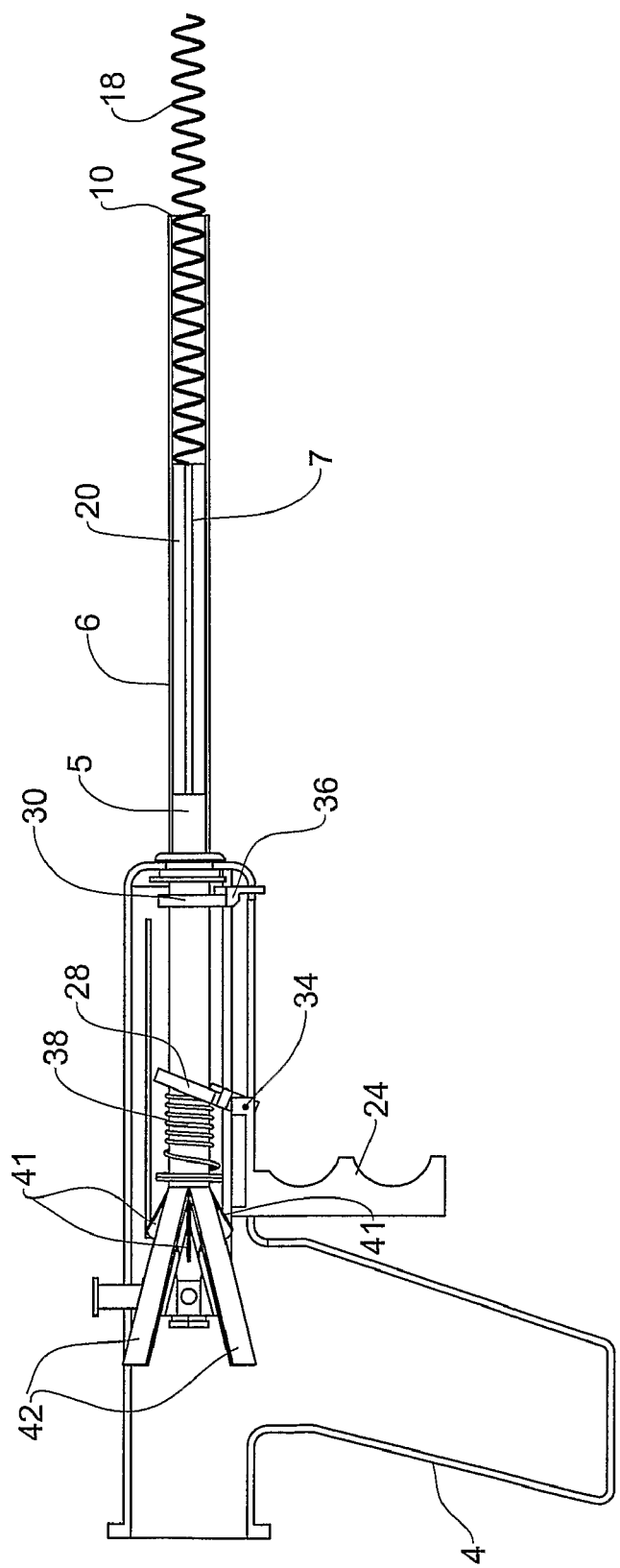
FIG. 3 shows the embodiment of FIGS. 1 and 2 in a later stage of actuation.

The friction clamp 28 is attached to the trigger 24 so that as the trigger 24 is depressed from its released position shown in FIG. 1 towards its depressed position shown in FIG. 3, the friction clamp 28 rotates around the pivot 34 in a clockwise direction in the perspective of FIGS. 1 to 3 from its straight position so as to firmly grasp the sheath 6 and cause the sheath 6 to be displaced proximally over the medical device 18, the spacer 20 and the tube 5. The distal end of the medical device thus becomes exposed as shown in FIGS. 2 and 3. The trigger 24 is spring biased in its released position by means of a helical spring 38 surrounding the sheath 6, so that when the trigger 24 in its depressed position (FIG. 3) is released, the trigger spontaneously slides to its released position (FIG. 1) under the influence of the spring 38. As the trigger 24 slides distally on the track 26 towards its released position, the friction clamp 28 rotates around the pivot 34, in a counterclockwise direction in the perspective of FIGS. 1 to 3, to its straight position. The sheath 6 is thus released from the grasp of the friction clamp 28 so that the sheath 6 is not pushed distally by the friction clamp 28 as it slides distally. Furthermore, as the trigger 24 slides distally towards its released position, the friction clamp 30 rotates around the pivot 36, in a clockwise direction in the perspective of FIGS. 1 to 3, to its tilted position and thus the friction clamp 30 prevents any distal movement of the sheath 6. Repeated cycles of depressing and releasing the trigger 24 therefore cause a cumulative sliding of the sheath 6 in a proximal direction.

As stated above the sheath 6 is made from a soft pliant material such as Teflon. As the sheath 6 slides proximally under the influence of the actuating mechanism 26, the proximal end 8 of the sheath 6 encounters one or more blades 41. The blades 41 are positioned in the grasping handle 4 so as to slit the sheath 6 longitudinally. The slit portion 42 of the sheath 6 splays apart allowing the slit portion 42 to pass around the fittings 12 and 14. The slit portion 42 may exit the grasping handle 4, as shown in FIGS. 2 and 3, or alternatively, may accumulate inside a compartment located inside the grasping handle. The proximal movement of the sheath 6 and the slitting of the proximal end of the sheath by the blades 41 continue until the sheath 6 has completely slid proximally over the medical device 18 so that the medical device 18 is no longer covered by the sheath 6 The medical device may then be deployed. For example, if the medical device 18 is a stent, the stent is deployed by being brought to its large caliber conformation. After deployment of the medical device 18, the sheath 6 is removed from the body.

Figure 4:
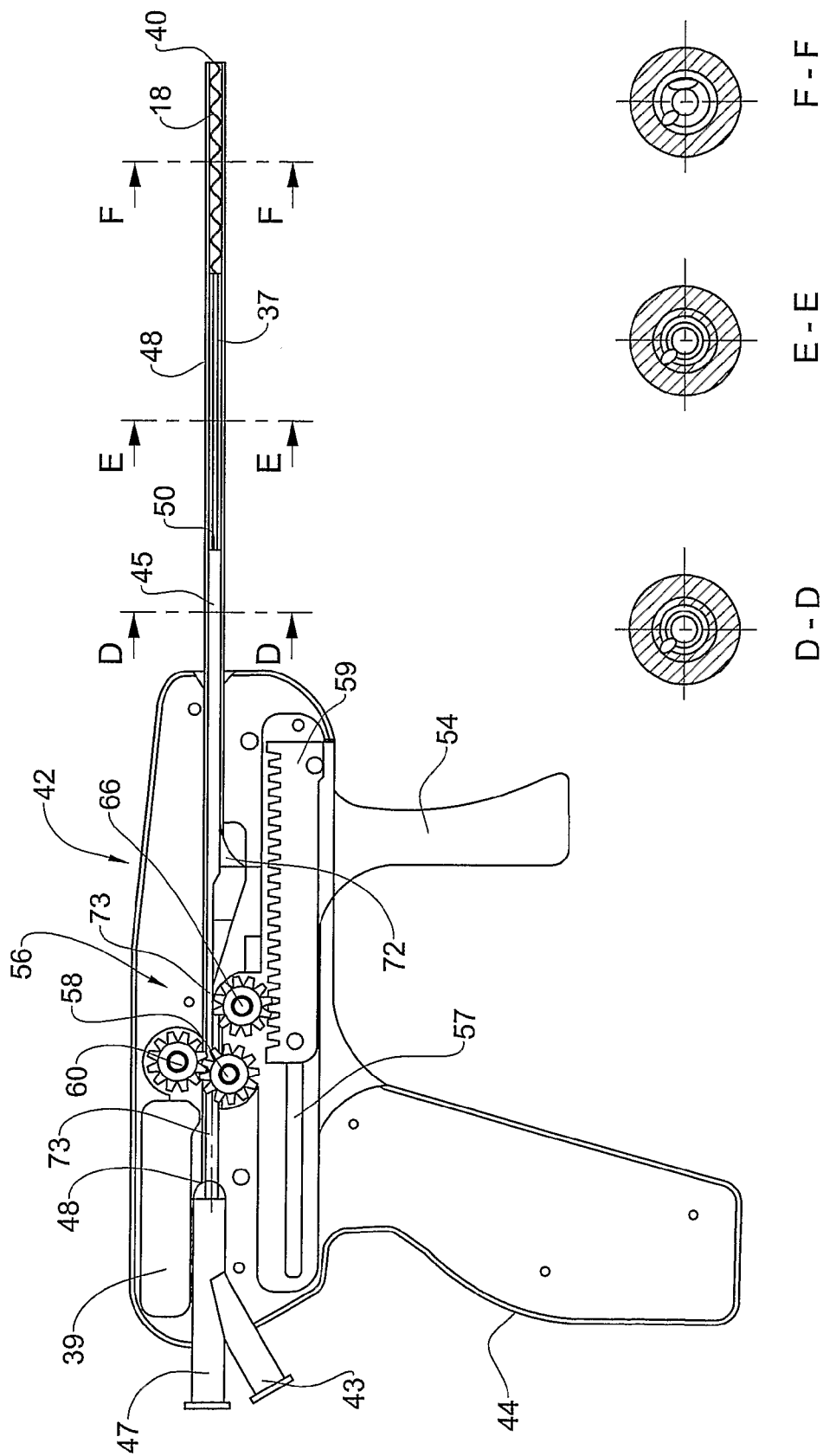
FIG. 4 shows a system for delivering a medical device to a body location according to a second embodiment of the invention.

FIG. 4 shows a delivery system 42 for delivering a medical device 18, such as a stent, to a body location, in accordance with another embodiment of the invention. Although the system 42 is shown with the medical device 18 being a stent, this is by way of example only, and the system 32 may be used to deliver any medical device such as an electrode, or a urethral shield.

Figure 7:
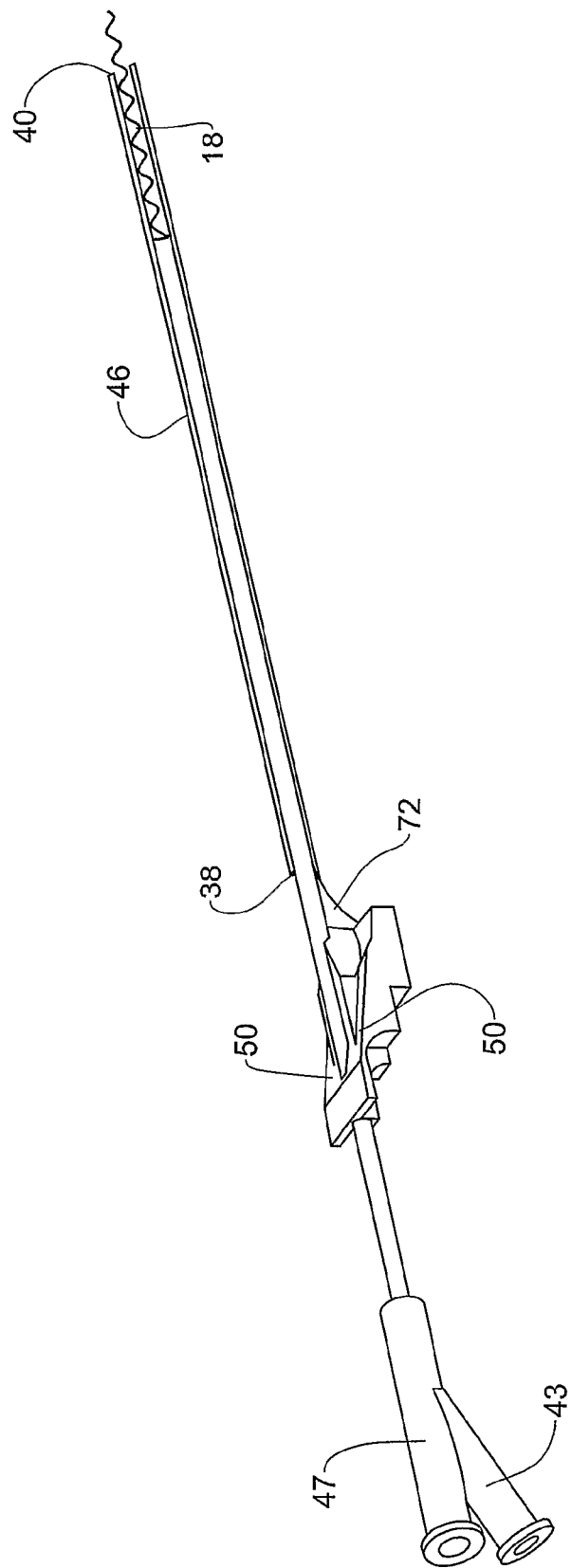
FIG. 7 shows slitting of a sheath by the embodiment of FIGS. 4 to 6.

The delivery system 42 has a grasping handle 44. A slender hollow sheath 46, having a proximal end 38 has an inner diameter configured to allow the medical device 18, such as a stent in its small caliber conformation or another medical device, to be contained inside the distal end of the sheath 46. In the case that the medical device 18 is a self-expanding stent, the sheath 46 may serve to restrain the stent in its narrow caliber configuration until it is to be deployed in the body. The sheath 46 is inserted over a tube 45 extending from the grasping handle 44, and is pushed towards one or more blades 72. In the lumen of the sheath 36, between the tip of the tube 35 and the medical device 18 is a spacing rod 50 having an axial channel 37. The tube 45 may be provided with a first fitting 43 for connection to a fluid source such as water or saline, for delivering the fluid to the distal end of the sheath 36 via the lumen of the tube 35 and the channel 37. The rigid tube 35 may also be provided with a second fitting 47 for attachment to an optical element (not shown) for viewing a body region in the vicinity of the distal end 40. FIG. 7 shows in a perspective view the arrangement of the tube 46, the one or more blades 72 and the fittings 43 and 47. As stated above the sheath 36 is made from a soft pliant material such as Teflon or polycarbonate. As the sheath 46 is pushed proximally, the proximal end 38 of the sheath 46 encounters the one or more blades 72. The blades 72 slit the sheath 46 longitudinally. The slit portion or portions 73 of the sheath 36 are guided by means of ramps 50 to pass between a gear 58 and a gear 60 (FIG. 5), as explained below.

Within the housing of the grasping handle 44, is an actuating mechanism, generally indicated by 56, for retracting the sheath 46 proximally so as to uncover the medical device 18, as explained in detail below.

When the medical device 18 has been delivered to a body location where it is to be deployed, the actuating mechanism 56 is used to retract the sheath 36 in a proximal direction so as to expose the medical device 18. The actuating mechanism 56 includes a trigger 54 that is slidable along a track 57 from a released position shown in FIG. 4, via an intermediate position shown in FIG. 5, to a depressed position shown in FIG. 6

The trigger 54 is attached to a gear rack 59. As the trigger 54 is moved proximally, it causes the gear 66 to rotate clockwise in the perspective of FIG. 5 by a rack and pinion mechanism and to slide proximally and engage the gear 58. Rotation of the gear 58 drives rotation of the gear 60. The slit portion 73 of the sheath 46 passes between the gears 58 and 60, and as the gears 58 and 60 rotate, the sheath 46 is driven proximally by the gears 58 and 60. The slit portion 73 may accumulate inside a compartment 39 located inside the grasping handle 34, as shown in FIGS. 4-6, or alternatively, may exit the housing of the grasping handle 44.

Figure 5:
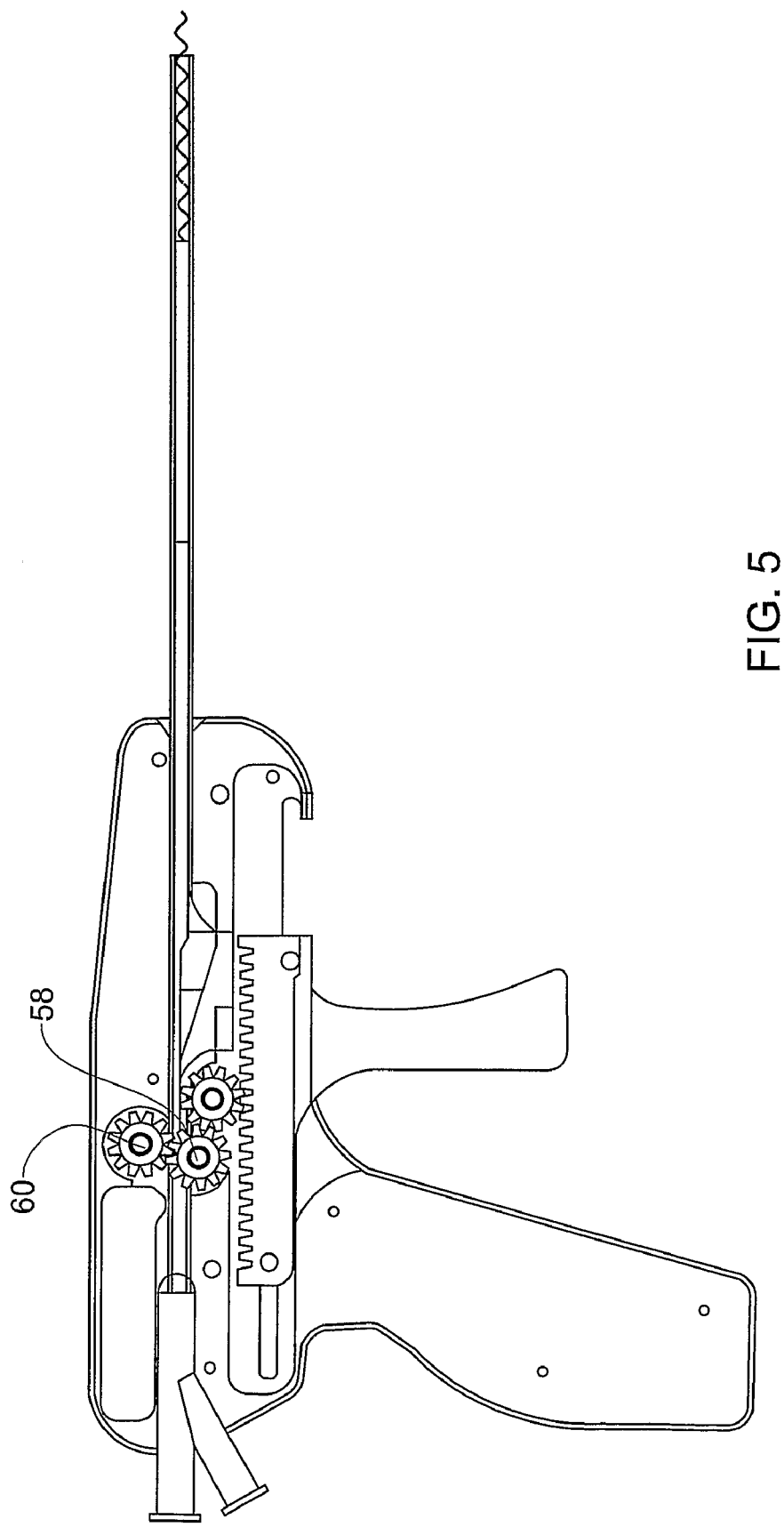
FIG. 5 shows the embodiment of FIG. 4 in an early stage of actuation.
Figure 6:
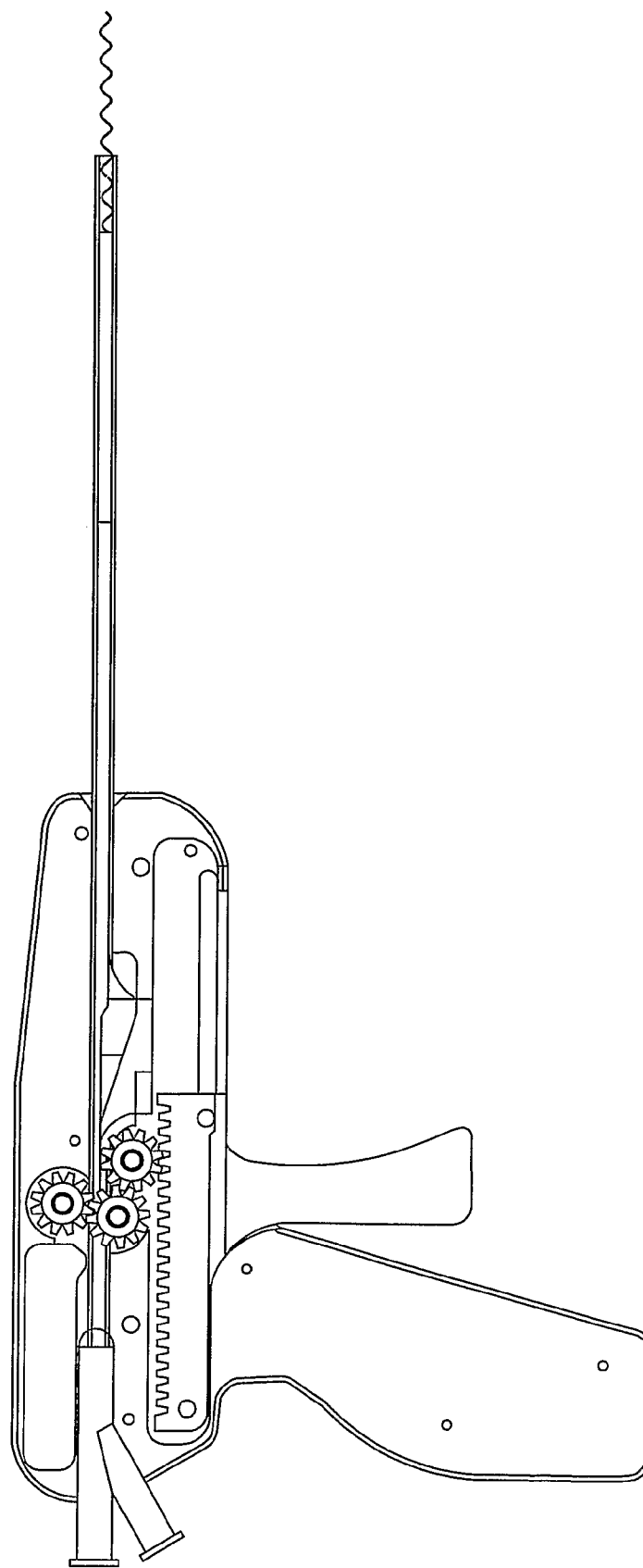
FIG. 6 shows the embodiment of FIGS. 4 and 5 in a later stage of actuation.

The trigger 54 is spring biased in its released position by a spring not seen in the perspective of FIGS. 4 to 6, so that when the trigger 54 in its depressed position (FIG. 6) is released, the trigger spontaneously slides to its released position (FIG. 4). As the trigger 54 slides distally towards its released position, it causes the gear 66 to rotate counterclockwise in the perspective of FIG. 5 and to slide distally by the rack and pinion mechanism so as to disengage from the gear 58 and release the grip of the slit portions 73 of the sheath 36. Thus, the sheath 46 is not pushed distally as the trigger 54 slides distally. Repeated cycles of depressing and releasing the trigger 54 therefore cause a cumulative sliding of the sheath 46 in a proximal direction.

The proximal movement of the sheath 46 and the slitting of the proximal end of the sheath by the blades 72 continue until the sheath 46 has completely slid proximally over the medical device 18 so that the medical device 18 is no longer covered by the sheath 46 The medical device may then be deployed. For example, if the medical device 18 is a stent, the stent is deployed by being brought to its large caliber conformation. After deployment of the medical device 18, the sheath 6 is removed from the body.

The invention claimed is:

1. A system for delivering a medical device to a body location, comprising:
   a handle;
   a sheath extending from the handle, the sheath having a proximal end and a distal end, the distal end being configured to receive the medical device;
   one or more blades secured within the handle; and
   an actuating mechanism coupled to the handle and capable of causing the sheath to slide proximally through the handle and be slit at its proximal end longitudinally by the one or more blades and to expose the medical device; wherein the actuating mechanism includes a trigger slidingly connected to the housing, the trigger having a released position and a depressed position, wherein movement of the trigger from its released position to its depressed position causes a proximal movement of the sheath; and wherein the actuating mechanism comprises one or more friction clamps, each friction clamp having a plate and the sheath passes through a hole in the plate, each friction clamp having an engaging position in which translation of the friction clamp is coupled with translation of the sheath, and a non-engaging position in which translation of the friction clamp is not coupled to translation of the sheath.

2. The delivery system according to claim 1 wherein the trigger is spring biased in its released position.

3. The delivery system according to claim 1 wherein a friction clamp assumes its engaging position when the trigger is moved from its released position to its depressed position so as to cause a proximal movement of the sheath.

4. The delivery system according to claim 1 wherein a friction clamp assumes its non-engaging position when the trigger is moved from its depressed position to its released position so as not to cause movement of the sheath.

5. The delivery system according to claim 1 wherein the plate is rotatable about a pivot between a non-engaging position in which movement of the plate is not coupled to movement of the sheath, and an engaging position in which movement of the plate is coupled to movement of the sheath.

6. The delivery system according to claim 5 wherein the plate assumes its engaging position when the trigger is moved from its released position to its depressed position.

7. The delivery system according to claim 6 wherein a plate assumes its non-engaging position when the trigger moves from its depressed position to its released position.

8. The delivery system according to claim 1 further comprising a spacer having a longitudinal channel, the spacer being located in the sheath between the actuating mechanism and the medical device.

9. The delivery system according to claim 1 further comprising a fitting adapted to be connected to a source of a pressurized fluid for delivering the fluid to the distal end of the sheath.

10. The delivery system according to claim 1 further comprising a fitting adapted to be connected to a viewing device for viewing the distal end of the sheath.

11. The delivery system according to claim 1 wherein the medical device is a stent, and electrode, or a uretral shield.

12. The delivery system according to claim 1 wherein the trigger is not rotatably connected to the housing.

13. A system for delivering a medical device to a body location, comprising:
   a handle;
   a sheath extending from the handle and formed from a soft pliant material, the sheath having a proximal end and a distal end, the distal end being configured to receive the medical device;
   one or more blades secured within the handle; and
   an actuating mechanism coupled to the handle, the actuating mechanism provided with:
      a trigger extending from the handle and configured to translate relative to the handle between a released position and a depressed position, and a friction clamp disposed within the handle and rotatably coupled to the trigger, the friction clamp having a plate with a hole formed therein such that the sheath passes through the hole, the friction clamp having an engaging position in which translation of the friction clamp is coupled with translation of the sheath, and a non-engaging position in which translation of the friction clamp is not coupled to translation of the sheath, wherein translation of the trigger from its released position to its depressed position rotates the friction clamp to engage the sheath and cause the sheath to slide proximally through the handle and be slit at its proximal end longitudinally by the one or more blades and to expose the medical device.

* * * * *